United States Patent
Doval et al.

(10) Patent No.: US 6,376,216 B1
(45) Date of Patent: Apr. 23, 2002

(54) PROMOTER FROM *ASHBYA GOSSYPII*

(75) Inventors: Jose Luis Revuelta Doval, Salamanca; Maria Angeles Santos Garcia, Salamanco, both of (ES); Markus Pompejus, Waldsee; Harald Seulberger, Neuhofen, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,041

(22) PCT Filed: Dec. 23, 1999

(86) PCT No.: PCT/EP98/08439

§ 371 Date: Jun. 21, 2000

§ 102(e) Date: Jun. 21, 2000

(87) PCT Pub. No.: WO99/33993

PCT Pub. Date: Jul. 8, 1999

(30) Foreign Application Priority Data

Dec. 23, 1997 (DE) .......................... 197 57 755

(51) Int. Cl.[7] ........................... C12P 21/06; C12N 1/14; C12N 15/74; C07H 21/04

(52) U.S. Cl. .................. 435/69.1; 435/254.11; 435/471; 536/23.1; 536/24.1

(58) Field of Search .............................. 536/23.1, 24.1; 435/254.11, 69.1, 471

(56) References Cited

U.S. PATENT DOCUMENTS 5,650,294 A 7/1997 Kurth et al. ............... 435/69.1

FOREIGN PATENT DOCUMENTS

WO 92/00379 1/1992

*Primary Examiner*—Robert A. Schwartzman
*Assistant Examiner*—Katharine F Davis
(74) *Attorney, Agent, or Firm*—Keil & Weinkauf

(57) ABSTRACT

A DNA sequence containing
a) the primary structure shown in SEQ ID NO:1 position 9 to 307 or
b) a primary structure which hybridizes with the double strand containing a) under standard conditions and which has essentially the same promoter activities as a) is suitable as promoter.

7 Claims, 2 Drawing Sheets

1 2 3 4 5 6

SEQUENCE LISTING

```
<160> NUMBER OF SEQ ID NOS: 1

<210> SEQ ID NO 1
<211> LENGTH: 315
<212> TYPE: DNA
<213> ORGANISM: Ashbya gossypii
<220> FEATURE:
<221> NAME/KEY: TATA_signal
<222> LOCATION: 224 ... 230
<221> NAME/KEY: misc_signal
<222> LOCATION: 43 ... 51
<221> NAME/KEY: misc_signal
<222> LOCATION: 77 ... 85

<400> SEQUENCE: 1
gcggccgctg tctgggtgca cgacacctga cctccgcccc gcggcttcct gttttcgccg      60
ggcgcggcaa tggtgcggct tcctccgaca ggaactacga cgaacggtca gcaccctgg     120 ggcccccacg ccgcaccaca gccgctgcgc gtgggcgtga aaattttac ctgcgggctc     180 tccttacgat ctctatttta tttcctgggg ggcagtcgaa atctatataa gagggcccg     240 ggacgcacaa cgggagactc tggtggagag accaggagtt tgaattaatt cagtccacac     300
atacacagcg gccgc                                                       315
```

PROMOTER FROM *ASHBYA GOSSYPII*

The present invention relates to a novel *Ashbya gossypii* promoter and its use for gene expression.

Filamentous fungi are important organisms for biotechnology owing to their characteristic of producing interesting constituents. These constituents which are formed by fungi include not only low-molecular-weight compounds such as organic acids, antibiotics or vitamins, but also higher-molecular-weight compounds such as enzymes, nonenzyme proteins or other biopolymers.

It is a general aim of biotechnology to optimize the production of such constituents by the fungi. Methods which are used to this end are, inter alia, also recombinant methods. These methods involve, for example, overexpressing individual genes or groups of genes in the filamentous fungus in question. These genes can be derived from the organism in which they are expressed, but also from other organisms.

In all cases, it is necessary to be able to govern the expression of the genes to be expressed. All the genes which are expressed in all organisms have a promoter region 5' of the encoding sequence. This region is responsible for the start of the transcription itself, and also for transcriptional regulation. As a rule, this regulation is done by binding transcription factors to regulatory sequences within the promoter region. As a rule, promoters are freely portable, i.e. a promoter of one gene may be used for governing the transcription of another gene. This governing of the new gene is then, as a rule, identical with the governing of the original gene from which the promoter is derived. Thus, known promoter whose regulation is known and can be governed can be used for governing in a known manner the expression of any gene.

The filamentous fungus *Ashbya gossypii* is of biotechnological and economic interest. It is particularly interesting owing to its characteristic of being able to produce large amounts of riboflavin (see, for example, Kurth et al. (1996) Riboflavin, in: Ullmann's Encyclopedia of Industrial Chemistry, VCH Weinheim). In addition, it is also interesting for the production of other metabolites and constituents. These constituents can be, for example, amino acids, vitamins, proteins, but also other substances of the primary and secondary metabolism, or other biopolymers.

The use of recombinant methods is promising for optimizing the production of such constituents in *Ashbya gossypii* and also in other organisms.

To carry out such an approach, genetic regulators (in particular promoters) of *Ashbya gossypii* itself are of great importance. Particularly interesting are those (so-called strong) promoters which make possible the overexpression of genes in *Ashbya gossypii*. Such strong promoters from Ashbya have not been described to date.

It is an object of the present invention to provide strong regulation elements for the transcription (promoters), which can principally be used in filamentous fungi, in particular those of the genus Ashbya.

A subject-matter of the invention is a DNA sequence which is suitable as promoter, containing
a) the primary structure shown in SEQ ID NO:1 position 9 to 307 or
b) a primary structure which hybridizes with the double strand containing a) under standard conditions and which has essentially the same promoter activities as a).

A promoter activity is termed essentially the same when the transcription of the A. gossypii GAP structural gene does not differ by more than 25%, preferably 10%, from a comparative value.

A particularly preferred promoter is the DNA sequence shown in SEQ ID NO:1 which at the 5' and 3' end has an NotI restriction cleavage site which is 8 nucleotides long in each case and which makes the promoter easily portable.

Important features for the function as promoter are:
the bona-fide TATA Box (nt 224–230), two sequence sections (nt 43–51 and 77–85) which correspond to the recognition sequence of the GCR1 binding element and
a sequence section (nt 9–20) whose complement partially corresponds to the recognition sequence of the RAPI binding element.

Subject-matter of the invention is also the use of the promoter sequences according to the invention in expression cassettes, where the promoter sequences are functionally linked to one or more structural genes. The term functional linkage describes such an arrangement of DNA sequences as to permit transcription of the structural gene(s).

Host organisms such as bacteria, yeasts, fungi, animals and plants can be transformed with the aid of such expression cassettes. Preferred host organisms are yeasts and fungi, in particular filamentous fungi like those of the genus Ashbya.

Subject-matter of the invention is also a method for the recombinant production of fine chemicals in host organisms, where a host organism is transformed with one of the expression cassettes described above, and this expression cassette contains one or more structural genes which encode the desired fine chemical or catalyze the biosynthesis of the desired fine chemical, the transformed host organism is cultured and the desired fine chemical is isolated from the culture medium.

This method is widely applicable to fine chemicals such as enzymes, vitamins, amino acids, sugars, fatty acids and natural and synthetic flavorings, aromas and colorants. The transformed host organisms are cultured and the fine chemical is isolated from the host organisms or the culture medium by methods known to the skilled worker.

The further embodiment of the invention is described in the examples which follow.

EXAMPLE 1

Generation of a Genomic Gene Library from *Ashbya gossypii* ATCC10895

Genomic DNA from *Ashbya gossypii* ATCC10895 can be prepared by customary methods, for example as described in EP 9703208. Starting from this DNA, the genomic gene library can be established by customary methods (for example Sambrook, J. et al. (1989) Molecular cloning: a laboratory manual, Cold Spring Harbor Laboratory Press or Ausubel, F. M. et al. (1994) Current protocols in molecular biology, John Wiley and sons) in any plasmid or cosmid, such as, for example, SuperCos1 (Stratagene, La Jolla, USA).

EXAMPLE 2

The *Ashbya gossypii* GAP Promoter

The *Ashbya gossypii* gene for glycerinaldehyde-3-phosphate dehydrogenase (AgGAP) can be cloned by means of a generally customary screening of a genomic *Ashbya gossypii* cosmid gene library (see EXAMPLE 1, using a probe generated from sequence information of the *Saccharomyces cerevisiae* GAP gene).

The 5' untranslated region of the gene (−373 to −8 region, in relation to the translation start) was assumed to be the promoter. Two cleavage sites for the restriction endonuclease NotI were introduced to flank this sequence. In this region, the bona-fide TATA box (nt 224–230), two sequence sections (nt 43–51 and 77–85) which correspond to the so-called GCR1 binding element and a sequence section (nt 9–20) whose complement partially corresponds to the *Saccharomyces cerevisiae* RAP1 binding element (see, for example, Johnston, M. and Carlson, M. (1992) pp.193–281in The molecular biology and cellular biology of the yeast Saccharomyces: Gene expression, Cold Spring Harbor Laboratory Press) are found in this region.

The promoter cassette which has thus been constructed can be placed upstream of any gene as a readily portable expression signal and leads to a marked overexpression of the respective gene in *Ashbya gossypii*, as is shown in EXAMPLE 3. The resulting sequence is the sequence of SEQ ID NO:1.

EXAMPLE 3

Construction of a Construct of the AgADE4 Gene with the *Ashbya gossypii* GAP Promoter, and Overexpression of the AgADE4 Gene in *Ashbya gossypii*.

To introduce the GAP promoter cassette 5' of the encoding region of AgADE4, a single NotI cleavage site (recognition sequence GCGGCCGC) was introduced by customary methods (for example Glover, D. M. and Hames, B. D. (1995) DNA cloning Vol.1, IRL press) 8 bp 5' of the ATG start codon.

The GAP promoter cassette (Example 2) can then be inserted into this position via NotI. A similar procedure can be followed when the GAP promoter cassette is cloned 5' of the encoding region of other *Ashbya gossypii* genes (such as, for example, the rib genes), but also when heterologous genes (i.e. those not derived from *Asbhya gossypii* such as, for example, genes for any enzymes) are cloned.

In *Ashbya gossypii*, the expression of the genes which carry the GAP promoter cassette 5' of the encoding region is controlled by the GAP promoter. This is shown by way of example in a Northern blot in FIG. 1.

BRIEF DESCRIPTION OF THE FIGURES

Description of FIG. 1

Northern blot of total *Ashbya gossypii* RNA with a fragment of AgADE4 (upper portion) or as internal constitutive control with the AgGPD1 gene (lower portion).

Figure 1:
Figure 1:
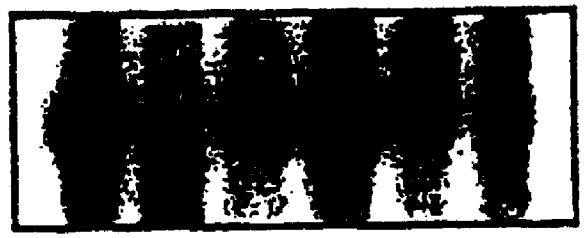
Figure 2:
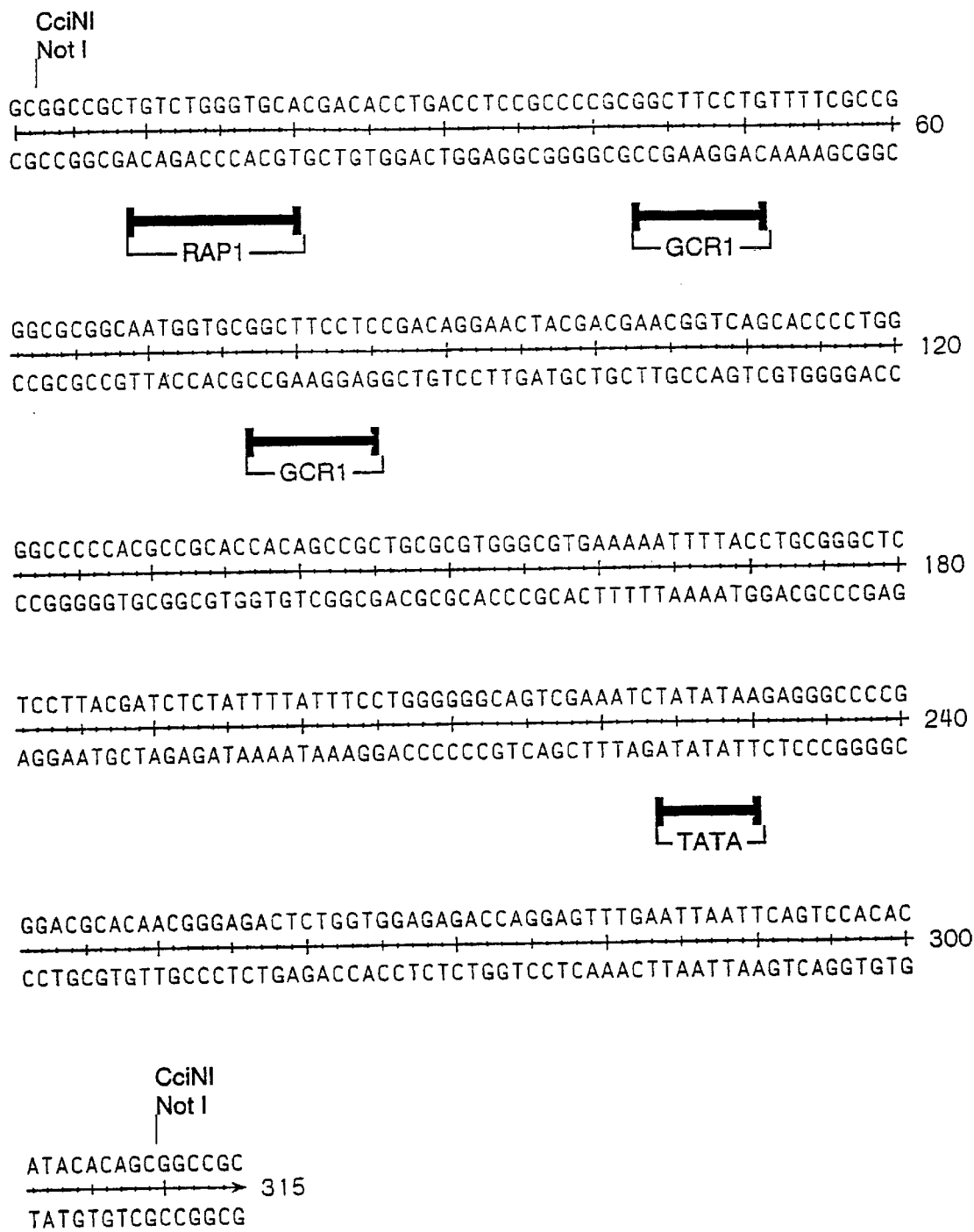

Lanes, left to right:

1. *Ashbya gossypii* RNA/wild type
2. *Ashbya gossypii* RNA/ade4::G418
3. *Ashbya gossypii* RNA/GAP-AgADE4
4. *Ashbya gossypii* RNA/GAP-AgADE4
5. *Ashbya gossypii* RNA/GAP-AgADE4-A418W
6. *Ashbya gossypii* RNA/GAP-AgADE4-D310V-K333A Description of FIG. 2:

*Ashbya gossypii* promoter (SEQ ID NO 1)

---

---

We claim:

1. An isolated DNA sequence which is suitable as a promoter, comprising a) the primary structure shown in SEQ ID NO:1 position 9 to 307.

2. The isolated DNA sequence as claimed in claim 1, comprising the primary structure shown in SEQ ID NO:1 position 1–315.

3. An expression cassette containing a DNA sequence as claimed in claim 1, functionally linked to at least one structural gene and, optionally, to other regulatory DNA sequences.

4. A method for expressing one or more genes in a filamentous fungus wherein the isolated DNA sequence of claim 1 is operably linked to one or more genes to form an expression cassette, the expression cassette is introduced into the filamentous fungus, and the filamentous fungus is incubated such that said one or more genes is expressed.

5. A method for the recombinant production of fine chemicals in filamentous fungus host organisms, wherein a filamentous fungus host organism is transformed with an expression cassette as claimed in claim 3, functionally linked to one or more structural genes coding for the desired fine chemical or for a protein that can catalyze the biosynthesis of the desired fine chemical, the transformed filamentous fungus host organism is cultured, and the desired fine chemical is isolated from the culture medium.

6. The method as claimed in claim 4 wherein the filamentous fungus is *Ashbya gossypii* and said one or more genes are endogenous or heterologous to *Ashbya gossypii*.

7. The method as claimed in claim 4 wherein said one or more genes are genes involved in purine metabolism.

* * * * *